United States Patent [19]

Miura

[11] Patent Number: 5,017,133

[45] Date of Patent: May 21, 1991

[54] ORTHODONTIC ARCHWIRE

[75] Inventor: Fujio Miura, Sakae, Japan

[73] Assignee: GAC International, Inc., Central Islip, N.Y.

[21] Appl. No.: 517,141

[22] Filed: May 1, 1990

[30] Foreign Application Priority Data

Jun. 20, 1989 [JP] Japan .............................. 1-71288[U]

[51] Int. Cl.⁵ ............................................. A61C 3/00
[52] U.S. Cl. .................................................. 433/20
[58] Field of Search ............................. 433/18, 20, 24

[56] References Cited

U.S. PATENT DOCUMENTS

| | | | |
|---|---|---|---|
| 4,037,324 | 7/1977 | Andreasen | 433/20 |
| 4,197,643 | 4/1980 | Burstone et al. | 433/20 |
| 4,412,819 | 11/1983 | Cannon | 433/20 |

Primary Examiner—John J. Wilson
Assistant Examiner—Cindy Cherichetti
Attorney, Agent, or Firm—Kenyon & Kenyon

[57] ABSTRACT

An orthodontic shape-memory alloy archwire for ligating to orthodontic appliances is heat treated, so that different sections of the archwire each exhibit a predetermined modulus of elasticity, and therefore impart a predetermined range of force when deflected. The distal ends of the archwire are further heat treated, or are treated with a dopant, to exhibit substantially diminished superelastic properties in comparison to the other sections of the archwire. The distal ends can therefore be deformed into shapes when ligated to orthodontic appliances to secure them to the appliances, and thus prevent them from slipping therethrough.

20 Claims, 2 Drawing Sheets

ORTHODONTIC ARCHWIRE

FIELD OF THE INVENTION

The present invention relates to orthodontic archwires and, in particular, to orthodontic archwires made of shape-memory alloy wires.

BACKGROUND INFORMATION

A variable force archwire made from a nickel-titanium (Ni-Ti) alloy wire is shown in Japanese utility model publication SHOO 63-34650 (1988). Different sections of the archwire are treated to develop different moduli of elasticity, thus imparting different forces when deflected. Typically, the sections corresponding to the front teeth, the bicuspids, and the molars are heat treated differently so that each section exhibits a unique modulus of elasticity. As a result, when the archwire is mounted to a patient's teeth, it imparts different forces to different sections of the dental arch.

A typical variable force archwire is heat treated so that its section corresponding to the molars imparts a greater force when deflected than its section corresponding to the bicuspids. The section corresponding to the bicuspids is typically heat treated to impart a greater force when deflected than the section corresponding to the front teeth.

One problem with non-variable force archwires is that the entire length of such an archwire exerts substantially the same force when deflected. Therefore, because it is necessary to impart different forces to different sections of a patient's dental arch, more than one archwire must be employed during the course of treatment. Typically, 7 to 8 different archwires may be used to treat a single patient. With variable force archwires, however, fewer archwires are required.

In FIG. 1, the teeth T of a typical dental arch are illustrated. An orthodontic archwire W is ligated to several orthodontic brackets B mounted to the teeth T. The bending and resultant tension within the archwire W creates forces that are imparted to the brackets B and thus the teeth T. The distal ends WA of the archwire W are secured to the brackets B mounted to the anterior molars, to prevent the archwire from slipping in the mesial direction.

With known stainless steel orthodontic archwires, the distal ends are typically bent into appropriate shapes to prevent them from slipping through the orthodontic brackets B. Typical stainless steel archwires are illustrated in FIGS. 2 and 3. As shown in FIG. 2, the distal end WA of the archwire W is formed into a triangular shape. In FIG. 3, the distal end WA is formed into a hook shape. The bent distal ends are often referred to as "stops".

One problem with shape-memory alloy archwires, such as Ni-Ti archwires, is that it has not been possible to bend their distal ends to form stops. Because of the properties of shape-memory alloy wires, when their distal ends are bent to form stops, the bent shapes are not retained because the archwires tend to return to their original shapes. It has been necessary therefore to attach fastening accessories to their distal ends to prevent them from slipping through the orthodontic appliances. For example, stop tubes are typically mechanically fastened to the distal ends of shape-memory alloy archwires. The procedure of attaching fastening accessories, however, has proven to be relatively complicated and time consuming.

It is an object of the present invention, therefore, to overcome the problems and disadvantages of known shape-memory alloy archwires.

SUMMARY OF THE INVENTION

The present invention is directed to an orthodontic shape-memory alloy archwire for ligating to orthodontic appliances. The archwire comprises a shape-memory alloy wire formed into an arch shape and heat treated so that at least one section of the archwire exhibits a predetermined modulus of elasticity and thus imparts a predetermined range of force when deflected. The distal ends of the archwire are treated to exhibit diminished superelastic properties in comparison to the at least one other section of the archwire. The distal ends are therefore deformable into shapes to prevent them from slipping through orthodontic appliances when mounted thereto.

The distal ends of one orthodontic shape-memory alloy archwire of the present invention are heat treated to exhibit diminished superelastic properties. A dopant is applied to the distal ends of another orthodontic shape-memory alloy archwire of the present invention. The dopant permits each distal end to be deformed and to retain the deformed shape, to prevent them from slipping through orthodontic appliances when mounted thereto. Preferably, the shape-memory alloy wire includes nickel titanium and the dopant includes iron.

The present invention is also directed to another orthodontic shape-memory alloy archwire. The archwire comprises a nickel titanium alloy wire formed into an arch shape. The section of the archwire corresponding to the front teeth is heat treated to exhibit a first predetermined modulus of elasticity. The sections corresponding to the bicuspids are heat treated to exhibit a second predetermined modulus of elasticity. The sections corresponding to the molars are heat treated to exhibit a third predetermined modulus of elasticity.

Each section of the archwire thus imparts a predetermined range of force when deflected. The distal ends of the archwire are heat treated to substantially diminish their superelastic properties in comparison to the other sections of the archwire. The distal ends are therefore deformable into shapes to secure them to orthodontic appliances when mounted thereto.

The present invention is also directed to a method of making an orthodontic shape-memory alloy archwire for mounting to orthodontic appliances. The method includes the following steps: forming a shape-memory alloy wire into an arch shape; heat treating the shape-memory alloy wire so that at least one section thereof exhibits a predetermined modulus of elasticity; and treating the distal ends of the archwire so that they no longer exhibit superelastic properties, or exhibit diminished superelastic properties in comparison to the at least one other section of the archwire. The distal ends are thus deformable into shapes to prevent them from slipping through orthodontic appliances when mounted thereto.

In one method of the present invention, the distal ends of the archwire are heat treated. The distal ends are preferably heat treated at a temperature within the range of about 600° C. to 900° C. In another method of the present invention, a dopant is applied to the distal ends of the archwire. The dopant preferably includes iron.

The present invention is also directed to another method of making an orthodontic shape-memory alloy archwire. The method comprises the following steps: heat treating the section of the archwire corresponding to the front teeth to impart a first predetermined range of force when deflected; heat treating the sections of the archwire corresponding to the bicuspids to impart a second predetermined range of force when deflected; heat treating the sections of the archwire corresponding to the molars to impart a third predetermined range of force when deflected; and heat treating the distal ends of the archwire to lose their superelastic properties, or to exhibit substantially diminished superelastic properties in comparison to the other sections of the archwire. The distal ends can therefore be deformed into shapes to secure them to orthodontic appliances.

In one method of the present invention, the distal ends of the archwire are heat treated at a temperature within the range of about 600° to 900° C. The section of the archwire corresponding to the front teeth is heat treated at a temperature within the range of about 400° C. to 600° C. for a time period within the range of about 1 hour to about 2.5 hours. The sections of the archwire corresponding to the bicuspids are heat treated at a temperature within the range of about 400° C. to 600° C. for a time period within the range of about 15 minutes to 1 hour. The sections of the archwire corresponding to the molars are heat treated at a temperature within the range of about 400° C. to 600° C. for a time period within the range of about 0 to 10 minutes.

One advantage of the present invention is that the distal ends of the archwire are treated so that they no longer exhibit superelastic properties, or exhibit substantially diminished superelastic properties. Therefore, the distal ends can be shaped to form stops in the same way as with stainless steel archwires. As a result, there is no need to fasten additional accessories to the distal ends of shape-memory alloy archwires, as previously done to prevent them from slipping through the orthodontic appliances.

Other advantages of the apparatus and method of the present invention will become apparent in view of the following detailed description and drawings taken in connection therewith.

DETAILED DESCRIPTION

Figure 4:
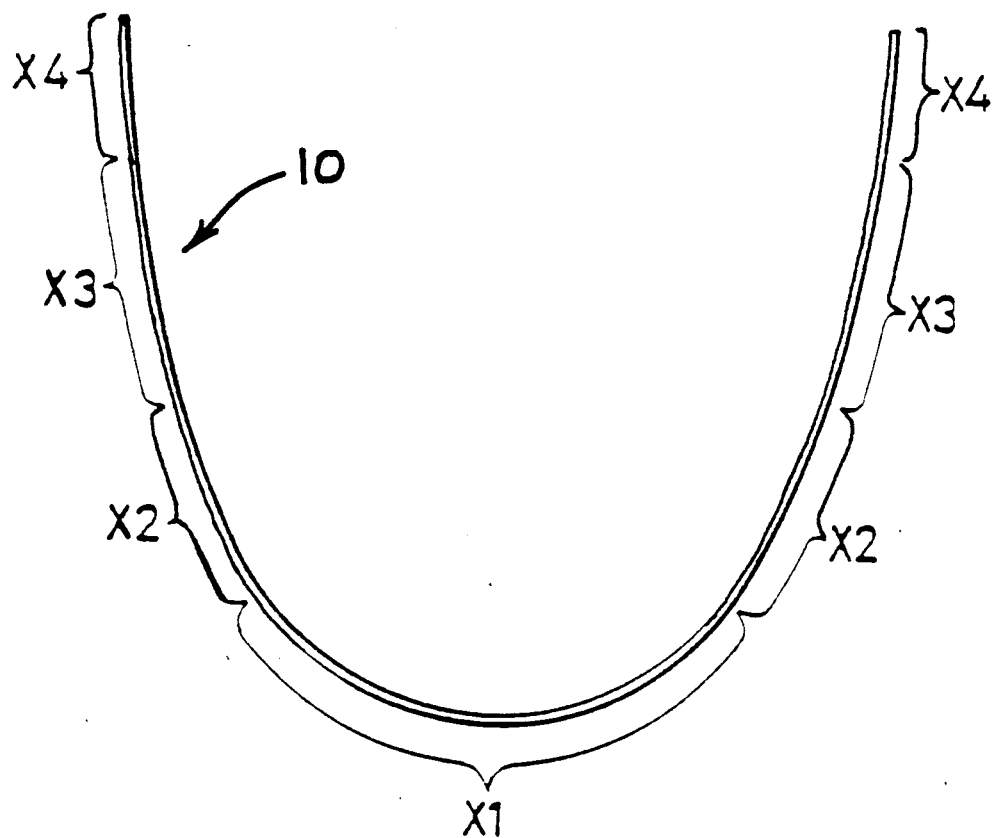
FIG. 4 is a top plan view of an orthodontic shape-memory alloy archwire embodying the present invention.

In FIG. 4, an orthodontic archwire embodying the present invention is indicated generally by the reference numeral 10. The archwire 10 is made of a shape-memory alloy wire, preferably a Ni-Ti alloy wire. The archwire 10 is heat treated so that different sections of the archwire exhibit unique moduli of elasticity. Each section therefore imparts a substantially predetermined force to the corresponding teeth of a dental arch.

The section X1 of the archwire 10 corresponds to the front teeth; the sections X2 correspond to the bicuspids; and the sections X3 correspond to the molars of a typical dental arch. The sections X4 are not used to impart forces, but are formed into stops to prevent the archwire from slipping through orthodontic appliances mounted to a patient's teeth, as described further below.

The archwire 10 is a variable force archwire, and therefore each of the sections X1 through X3 is heat treated to exhibit a unique modulus of elasticity. Each respective modulus of elasticity is selected so that the respective section of the archwire imparts a substantially predetermined force to the corresponding teeth of a dental arch. The section X1 is heat treated to impart an optimal range of force to the front teeth; the sections X2 are heat treated to impart an optimal range of force to the bicuspids; and the sections X3 are heat treated to impart an optimal range of force to the molars.

In accordance with one embodiment of the present invention, the archwire 10 is made of a Ni-Ti alloy wire having a 0.016 inch wire diameter. Sections X1, X2 and X3 of the archwire are each heat treated to exhibit a unique modulus of elasticity. Sections X4, on the other hand, are initially heat treated in the same way as sections X3, so that they exhibit substantially the same modulus of elasticity.

The section X1 is heat treated in a conventional heating solution at about 500° C. for a time period within the range of about 60 to 80 minutes. While the section X1 is heat treated, the other sections of the archwire, X2 through X4, are not immersed in the heating solution but are maintained at a lower temperature. Then, both sections X1 and X2 are immersed in the heating solution, which is again maintained at about 500° C., for a time period within the range of about 25 to 35 minutes. The entire archwire 10 is then immersed in the heating solution, which is still maintained at about 500° C., for approximately 5 minutes. The archwire 10 is then removed from the heating solution and permitted to cool to room temperature.

Thus, the section X1 of the archwire 10, which corresponds to the front teeth, is heat treated at about 500° C. for a total time period within the range of about 90 minutes to about 2 hours. The sections X2, which correspond to the bicuspids, are heat treated at about 500° C. for a time period within the range of about 30 minutes to about 40 minutes. The sections X3, which correspond to the molars, and the sections X4, which are used to form stops, are heat treated at about 500° C. for about 5 minutes. Therefore, sections X1, X2 and X3 of the archwire 10 are each heat treated to exhibit a unique modulus of elasticity. Sections X4, on the other hand, are heat treated in the same way as sections X3, and thus should exhibit about the same modulus of elasticity.

The different sections of the archwire 10 exhibited the following loads when deflected about 2 mm: section X1 imparted loads within the range of about 30 grams ("G") to 70 G; sections X2 imparted loads within the range of about 140 G to 170 G; and sections X3 imparted loads within the range of about 250 G to 280 G.

The sections X4 are then treated again so that they no longer exhibit superelastic properties, or exhibit substantially diminished superelastic properties. Once the sections X4 lose their superelastic properties, or exhibit only negligible superelastic properties, they can be formed into stops in the same way as with stainless steel archwires.

There are various methods for finally treating the sections X4. One method is to immerse them into a conventional heating solution, maintained within a temperature range of about 700° C. to 800° C. The other sections of the archwire 10 are not immersed in the heating solution, but are maintained at substantially lower temperatures. The sections X4 are maintained in the heating solution for a time period so that they no longer exhibit superelastic properties, or exhibit substantially diminished superelastic properties.

Another method is to heat treat the sections X4 by using a pair of electric pliers (not shown). The electrodes of the pliers are gripped on either end of each section X4, so that the electric current can pass through each section. The level of electric current is selected so that each section X4 is heated to a temperature within the range of about 700° C. to 800° C. The sections X4 are heated for a period of time so that they no longer exhibit superelastic properties, or exhibit significantly diminished superelastic properties.

Figure 1:
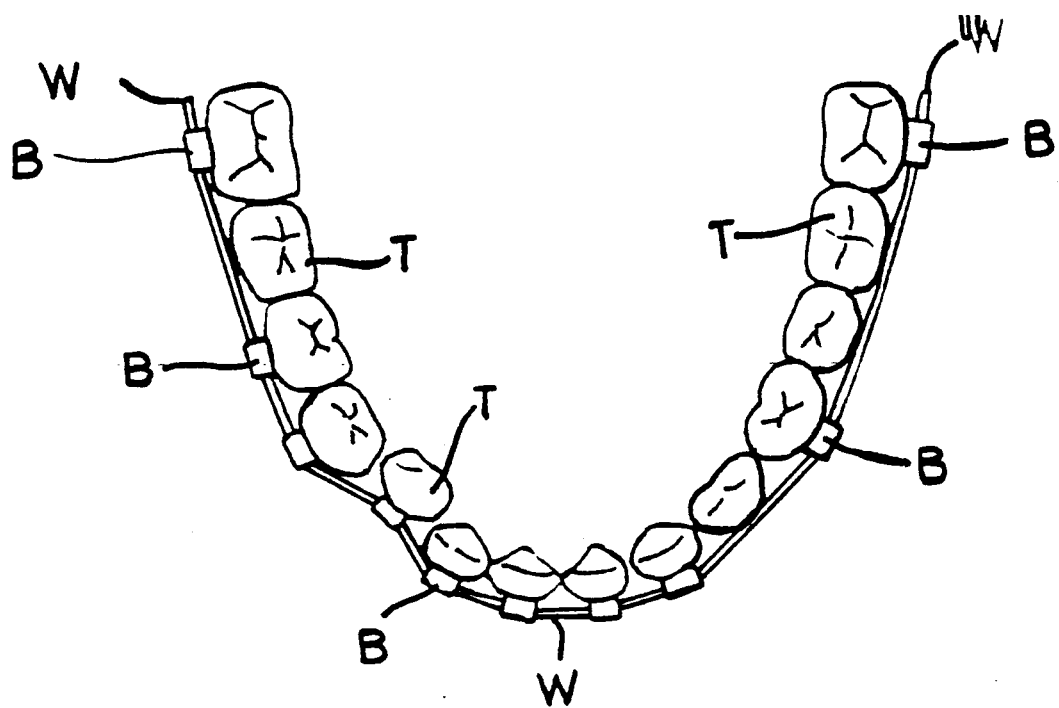
FIG. 1 is a top plan view of the teeth of a typical dental arch having orthodontic brackets and an archwire mounted thereto.
Figure 2:
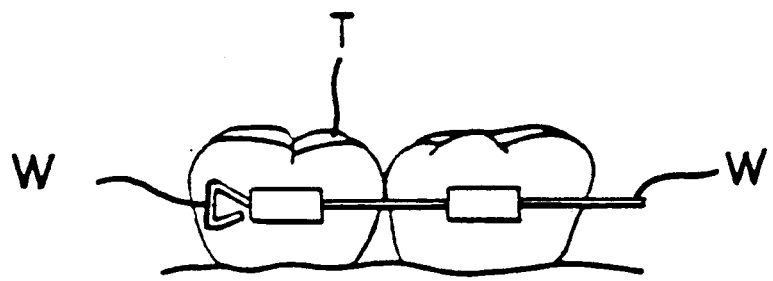
FIG. 2 is a side plan view of the distal end of a stainless steel archwire mounted to the teeth of a dental arch.
Figure 3:
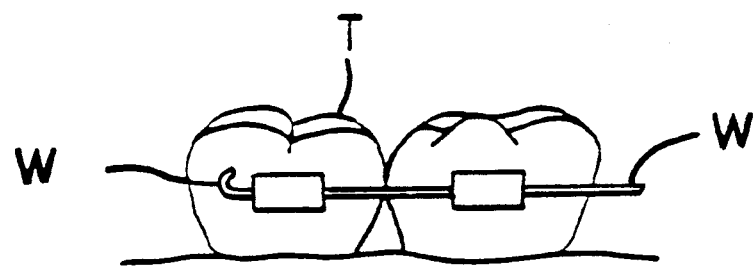
FIG. 3 is a side plan view of the distal end of another stainless steel archwire mounted to the teeth of a dental arch.

Another method is to treat each section X4 with a dopant, such as iron ions (Fe). The iron permits the sections X4 to be bent and to maintain the bent shape, by preventing the shape-memory alloy wire from returning to its original shape. Once the sections X4 are finally treated, they can be formed into stops in the same manner as with stainless steel archwires. For example, the finally treated sections X4 can be formed into the shapes shown in either FIGS. 2 or 3.

One advantage of the present invention, is that there is no need to fasten additional accessories to the distal ends of shape-memory alloy archwires, as previously done to prevent them from slipping through the orthodontic appliances. Because the sections X4 of the archwire 10 are treated so that they no longer exhibit superelastic properties, or exhibit substantially diminished superelastic properties, they can be shaped to form stops in the same way as with stainless steel archwires.

I claim:

1. An orthodontic shape-memory alloy archwire for ligating to orthodontic appliances, comprising:
   a shape-memory alloy wire formed into an arch shape and exhibiting superelastic properties for imparting a substantially constant force upon deflection within a patient's mouth, the shapememory alloy wire being heat treated so that at least one section of the archwire exhibits a predetermined modulus of elasticity and thus imparts a predetermined range of force when deflected,
   the distal ends of the archwire being treated to exhibit substantially diminished superelastic properties in comparison to the at least one other section of the archwire, the distal ends thus being deformable into shapes to prevent them from slipping through orthodontic appliances when mounted thereto.

2. An orthodontic shape-memory alloy archwire as defined in claim 1, wherein
   the distal ends are heat treated to exhibit diminished superelastic properties.

3. An orthodontic shape-memory alloy archwire as defined in claim 1, further comprising:
   a dopant applied to the distal ends thereof, the dopant permitting each distal end to be deformed and to retain the deformed shape.

4. An orthodontic shape-memory alloy archwire as defined in claim 3, wherein
   the shape-memory alloy wire includes Ni-Ti and the dopant includes iron.

5. A method of making an orthodontic shape-memory alloy archwire for mounting to orthodontic appliances, comprising the following steps:
   forming a shape-memory alloy wire into an arch shape;
   heat treating the shape-memory alloy wire so that at least one section thereof exhibits a predetermined modulus of elasticity; and
   treating the distal ends of the archwire so that they no longer exhibit superelastic properties, or exhibit diminished superelastic properties in comparison to the at least one other section of the archwire, the distal ends thus being deformable into shapes to prevent them from slipping through orthodontic appliances when mounted thereto.

6. A method of making an orthodontic shape-memory alloy archwire as defined in claim 5, wherein
   the distal ends are heat treated.

7. A method of making an orthodontic shape-memory alloy archwire as defined in claim 6, wherein
   the distal ends are heat treated at a temperature within the range of about 600° C. to 900° C.

8. A method of making an orthodontic shape-memory alloy archwire as defined in claim 5, wherein
   a dopant is applied the distal ends of the archwire.

9. A method of making an orthodontic shape-memory alloy archwire as defined in claim 8, wherein
   the dopant includes iron.

10. An orthodontic shape-memory alloy archwire for ligating to orthodontic appliances, comprising:
    a shape-memory alloy wire formed into an arch shape and exhibiting superelastic properties for imparting a substantially constant force upon deflection when mounted to a patient's teeth, the distal ends of the archwire being treated to substantially diminish their superelastic properties in comparison to the other sections of the archwire, the distal ends thus being deformable into shapes to secure them to orthodontic appliances when mounted thereto.

11. An orthodontic shape-memory alloy archwire as defined in claim 10, wherein
    the distal ends are heat treated.

12. An orthodontic shape-memory alloy archwire as defined in claim 10, wherein
    the distal ends are treated with a dopant.

13. An orthodontic shape-memory alloy archwire, comprising:
    a Ni-Ti alloy wire formed into an arch shape and exhibiting superelastic properties for imparting a substantially constant force upon deflection within a patient's mouth, the section of the archwire corresponding to the front teeth being heat treated to exhibit a first predetermined modulus of elasticity, the sections corresponding to the bicuspids being heat treated to exhibit a second predetermined modulus of elasticity, and the sections corresponding to the molars being heat treated to exhibit a third predetermined modulus of elasticity, each section of the archwire thus imparting a predetermined range of force when deflected, and
    the distal ends of the archwire being heat treated to substantially diminish their superelastic properties in comparison to the other sections of the archwire, the distal ends thus being deformable into shapes to secure them to orthodontic appliances when mounted thereto.

14. A method of making an orthodontic shape-memory alloy archwire, comprising the following steps:

heat treating the section of the archwire corresponding to the front teeth to impart a first predetermined range of force when deflected;

heat treating the sections of the archwire corresponding to the bicuspids to impart a second predetermined range of force when deflected;

heat treating the sections of the archwire corresponding to the molars to impart a third predetermined range of force when deflected; and heat treating the distal ends of the archwire to lose their superelastic properties, or to exhibit substantially diminished superelastic properties in comparison to the other sections of the archwire, to permit the distal ends to be deformed into shapes to secure them to orthodontic appliances.

15. A method of making an orthodontic shape-memory alloy archwire as defined in claim 14, wherein
the distal ends of the archwire are heat treated at a temperature within the range of about 600° to 900° C.

16. A method of making an orthodontic shape-memory alloy archwire as defined in claim 15, wherein
the section of the archwire corresponding to the front teeth is heat treated at a temperature within the range of about 400° C. to 600° C. for a time period within the range of about one hour to about 2.5 hours;

the sections of the archwire corresponding to the bicuspids are heat treated at a temperature within the range of about 400° C. to 600° C. for a time period within the range of about 15 minutes to 1 hour; and the sections of the archwire corresponding to the molars are heat treated at a temperature within the range of about 400° C. to 600° C. for a time period within the range of about 0 to 10 minutes.

17. An orthodontic shape-memory alloy archwire for ligating to orthodontic appliances, comprising:
a Ni-Ti alloy wire formed into an arch shape and exhibiting superelastic properties for imparting a substantially constant force upon deflection thereof when mounted to teeth, the sections of the archwire corresponding to the front teeth, the bicuspids, and the molars of a dental arch, each being heat treated differently than the others, and thus exhibiting a different modulus of elasticity than the others, and the distal ends of the archwire being heat treated at a temperature within the range of about 600° to 900° C. to substantially diminish their superelastic properties in comparison to the other sections of the archwire, the distal ends thus being deformable into shapes to secure them to orthodontic appliances.

18. An orthodontic shape-memory alloy archwire as defined in claim 17, wherein
the sections of the archwire corresponding to the front teeth have been heat treated at a temperature within the range of about 400° C. to 600° C. for a time period within the range of about one hour to about 2.5 hours;

the sections of the archwire corresponding to the bicuspids have been heat treated at a temperature within the range of about 400° C. to 600° C. for a time period within the range of about 15 minutes to 1 hour; and the sections of the archwire corresponding to the molars have been heat treated at a temperature within the range of about 400° C. to 600° C. for a time period within the range of 0 to 10 minutes.

19. An orthodontic shape-memory alloy archwire for ligating to orthodontic appliances,
a Ni-Ti alloy wire formed into an arch shape and exhibiting superelastic properties for imparting a substantially constant force upon deflection thereof when mounted to teeth, the sections of the archwire corresponding to the front teeth, the bicuspids, and the molars of a dental arch, each being heat treated differently than the others, and thus exhibiting a different modulus of elasticity than the others, and the distal ends of the archwire including an iron dopant thereon, the distal ends thus being deformable into shapes to secure them to orthodontic appliances.

20. An orthodontic shape-memory alloy archwire for ligating to orthodontic appliances, comprising:
a shape-memory alloy wire formed into an arch shape and exhibiting superelastic properties for imparting a substantially constant force upon deflection within a patient's mouth, an anterior section of the archwire being heat treated to exhibit a first predetermined modulus of elasticity, and at least one posterior section of the archwire being heat treated to exhibit a second predetermined modulus of elasticity, the distal ends of the archwire being heat treated to substantially diminish their superelastic properties in comparison to the other sections of the archwire, the distal ends thus being deformable into shapes to fix them relative to orthodontic appliances when mounted thereto.

* * * * *